(12) United States Patent
Kawula et al.

(10) Patent No.: US 11,382,492 B2
(45) Date of Patent: Jul. 12, 2022

(54) WIRELESS ENDOSCOPIC SURGICAL DEVICE

(71) Applicant: Scopernicus, LLC, Stanhope, NJ (US)

(72) Inventors: Paul John Kawula, Sunnyvale, CA (US); James McAvinn, Stanhope, NJ (US); Patrick T. Walsh, Cranford, NJ (US)

( * ) Notice: Subject to any disclaimer, the term of this patent is extended or adjusted under 35 U.S.C. 154(b) by 0 days.

(21) Appl. No.: 16/933,786

(22) Filed: Jul. 20, 2020

(65) Prior Publication Data

US 2020/0375435 A1 Dec. 3, 2020

Related U.S. Application Data

(63) Continuation-in-part of application No. 15/094,992, filed on Apr. 8, 2016, now abandoned, which is a continuation-in-part of application No. 13/759,920, filed on Feb. 5, 2013, now abandoned.

(51) Int. Cl.
| | |
|---|---|
| *A61B 1/06* | (2006.01) |
| *A61B 1/04* | (2006.01) |
| *A61B 1/018* | (2006.01) |
| *A61B 1/00* | (2006.01) |
| *A61B 1/07* | (2006.01) |

(52) U.S. Cl.
CPC ...... *A61B 1/00108* (2013.01); *A61B 1/00006* (2013.01); *A61B 1/00016* (2013.01); *A61B 1/00066* (2013.01); *A61B 1/018* (2013.01); *A61B 1/042* (2013.01); *A61B 1/0669* (2013.01); *A61B 1/0684* (2013.01); *A61B 1/07* (2013.01)

(58) Field of Classification Search
USPC .................................................. 385/117, 119
See application file for complete search history.

(56) References Cited

U.S. PATENT DOCUMENTS

| | | | | |
|---|---|---|---|---|
| 3,556,085 | A | * | 1/1971 | Takahashi .......... A61B 1/00165 600/129 |
| 3,889,662 | A | * | 6/1975 | Mitsui ................ A61B 1/00195 600/139 |
| 4,261,346 | A | * | 4/1981 | Wettermann ........... A61B 1/313 600/104 |
| 4,267,828 | A | * | 5/1981 | Matsuo ............... A61B 1/00165 385/117 |
| 4,273,110 | A | * | 6/1981 | Groux .................... A61B 1/002 600/156 |
| RE32,158 | E | * | 5/1986 | Vukovic ................ A61B 1/015 600/123 |

(Continued)

*Primary Examiner* — John P Leubecker
(74) *Attorney, Agent, or Firm* — Charles Runyan; Runyan Law

(57) ABSTRACT

An endoscopic surgical device used for minimally invasive procedures comprises a handheld component and a power control module. The handheld component consisting of a handle, and a conduit houses a wireless imaging module and a single LED light source. The imaging module comprises a wired or wireless camera coupled to an optically folded assembly or imaging assembly. A battery-operated power module can control both the intensity of the LED and the camera action. The handle and conduit are designed to accommodate surgical tools, wherein the imaging model is parallel offset to the tool, or the tool are parallel offset to the imaging. In alternative embodiments, the handheld component is self-contained.

17 Claims, 7 Drawing Sheets

(56) References Cited

U.S. PATENT DOCUMENTS

| | | | |
|---|---|---|---|
| 4,676,592 A * | 6/1987 | Nishioka | G02B 23/26 385/117 |
| 4,753,510 A | 6/1988 | Sezerman | |
| 4,802,460 A * | 2/1989 | Ohkuwa | A61B 1/00096 385/117 |
| 4,916,534 A | 4/1990 | Takhashi et al. | |
| 5,785,644 A * | 7/1998 | Grabover | A61B 1/00052 600/109 |
| 5,928,137 A | 7/1999 | Green | |
| 6,141,037 A | 10/2000 | Upton | |
| 6,221,007 B1 * | 4/2001 | Green | A61B 1/00052 600/104 |
| 6,371,909 B1 * | 4/2002 | Hoeg | A61B 1/00096 600/112 |
| 6,498,884 B1 * | 12/2002 | Colvin | A61B 1/00167 348/E5.029 |
| 6,545,260 B1 * | 4/2003 | Katashiro | G01B 9/00 250/227.26 |
| 8,317,689 B1 | 11/2012 | Remijan et al. | |
| 2002/0120181 A1 * | 8/2002 | Irion | G02B 27/145 600/178 |
| 2003/0156788 A1 * | 8/2003 | Henning | A61B 5/0088 385/31 |
| 2003/0214579 A1 | 11/2003 | Iddan | |
| 2005/0143626 A1 | 6/2005 | Prescott | |
| 2005/0182342 A1 | 8/2005 | Dinsmoor et al. | |
| 2005/0283048 A1 | 12/2005 | Gill et al. | |
| 2006/0041193 A1 | 2/2006 | Wright et al. | |
| 2006/0211918 A1 | 9/2006 | Lieponis | |
| 2008/0064925 A1 | 3/2008 | Gill et al. | |
| 2008/0108011 A1 * | 5/2008 | Nahlieli | A61M 1/0058 433/29 |
| 2008/0177177 A1 | 7/2008 | Aoki et al. | |
| 2011/0018988 A1 * | 1/2011 | Kazakevich | A61B 1/042 348/68 |
| 2011/0193948 A1 | 8/2011 | Amling et al. | |
| 2013/0071077 A1 * | 3/2013 | Demers | A61B 1/00009 385/117 |
| 2013/0102846 A1 | 4/2013 | Sjostrom et al. | |
| 2013/0135614 A1 | 5/2013 | Wax et al. | |
| 2013/0204084 A1 | 8/2013 | Hale et al. | |
| 2013/0296649 A1 | 11/2013 | Kirma et al. | |
| 2015/0215614 A1 * | 7/2015 | Witt | H04N 13/398 348/45 |
| 2015/0297062 A1 * | 10/2015 | Golenberg | A61B 90/37 348/68 |
| 2016/0235276 A1 * | 8/2016 | Steffen | A61B 90/20 |
| 2019/0159662 A1 * | 5/2019 | Papas | A61B 1/07 |

* cited by examiner

WIRELESS ENDOSCOPIC SURGICAL DEVICE

REFERENCE TO RELATED REFERENCES

This application is a Continuation-in-Part of U.S. patent application Ser. No. 15/094,992, filed on Apr. 8, 2016, abandoned, which is a Continuation-in-Part of U.S. patent application Ser. No. 13/759,920, filed on Feb. 5, 2013, abandoned; the contents of both applications are incorporated by reference in their entirety.

FIELD OF THE INVENTION

The field of the invention generally relates to minimally invasive surgical and interventional endoscopic devices and methods. More particularly, the field of the invention relates to tool-bearing endoscopes for endoscopic or robotic surgical procedures in general, cardiac, thoracic, endovascular, urologic, gynecologic, colorectal, oncologic, endocrine, pediatric, head and neck, hand, metabolic, and bariatric laparoscopic surgery; and minimally invasive orthopedic and neurological surgery, as well as for vascular access surgical procedures and methods of vessel harvesting during cardiac surgery.

BACKGROUND OF THE INVENTION

Minimally invasive surgery has many benefits for patients in that the incisions are much smaller, which helps prevent wound infections, incisional hernias, and better cosmesis. Endoscopes are used to view the inside of the body through a small incision during minimally invasive surgery. Generally, this requires the surgeon to work in small spaces, with an endoscope placed in a separate port and instruments frequently coming from different directions through numerous other small ports. For single-port surgery, the challenges are compounded by the necessity to share the single incision with both an endoscope and one or more instruments. The visualization port is the same as the working port.

Conventional surgical endoscopes are used in a variety of minimally invasive surgical procedures and are typically inserted into the body through an incision, called a port. Typically, endoscopes are standalone instruments and do not have channels for tools, called tool bores. Tools are generally placed through separate port incisions. In most surgical procedures, there are multiple ports, one for the endoscope and one or more separate ports for surgical tools, such as energy devices, clamps, retractors, etc. In the case of single incision laparoscopic surgery, the surgeon can use a multi-instrument access port platform (ex., GELPOINT from Applied Medical and SILS PORT from Medtronic) that typically is placed through or next to the umbilicus. This technique has declined in popularity because of issues related to the 'sword fighting' of instruments going through a common entry point. In multi-port abdominal laparoscopic surgery, the umbilical or periumbilical port is used for placement of the endoscope, which is also the preferred port for specimen removal. Specimen (ex., gall bladder) removal through these ports requires the surgeon to remove the endoscope first. But the surgeon must still view the mobilization, cutting, clamping, and placement of the specimen in the bag before removal. To remove the specimen from the body, surgeons typically remove the endoscope from the umbilical port and place a smaller diameter endoscope in an ancillary port. These manipulations allow the surgeon to capture the specimen in a bag and remove it through the umbilical port while using the endoscope in the ancillary port to view the specimen.

In the case of endoscopic vein harvesting (EVH) or endoscopic radial artery harvesting for coronary artery bypass surgery, the endoscope is inserted into the proximal end of a harvesting cannula. The surgical cauterizing and transection tool enters the cannula from the side. The disadvantage of this approach is that during the harvesting procedure, side entry creates increased torque and excessive stiction forces during manipulation of the tool, which can cause tool breakage. These unwarranted forces occur because the tool is not parallel to the endoscope along its entire length. Moreover, side entry requires the endoscope to redirect the tip of the tool, using a plate inside of the endoscope to supply the redirection force. The plate can cause the top of the tool to hang or catch on the plate. Also, the surgical device moving across the redirection plate can grind off tip or plate material, which is frequently left in the patient.

Imaging systems in minimally invasive surgical procedures consist of a chain of devices: endoscope, camera head, video signal processor, video cable, monitor, light source, and fiber-optic cable. This chain forms cord clutter. So much equipment requires so many equipment boxes that the suite must have a storage rack, further using up valuable space in overcrowded operating rooms.

Light sources in a video endoscopy unit require a hot, bright light source, such as a halogen, metal halide, or xenon bulb. There is a fiber-optic cable from the light source to the fiber-optic bundle in the endoscope. Broken bundles can lead to degraded image quality and require its replacement. Camera systems have a camera head that attaches to the endoscope by a coupler, and the camera head is attached to a camera control box. An alternative configuration is to have a charge-coupled device (CCD) chip at the end of the endoscope that plugs into a video signal-processing box.

Generally, endoscope optics are inline. Endoscopes bend the image path to allow viewing angles different from tool bore angles. US Pat. Application No. US 2008/0108011 discusses such technologies and discloses an endoscope for root canal treatment. In this endoscope, the tool bore's longitudinal axis may sit at any suitable angle, about 45° to about 135°, to the imaging or handpiece axis. This bend requires a prism or mirror to transmit the image from the tool bore axis to the handpiece axis. However, in the case of a 0° angle, this patent application states that no optical folded path is needed: if the optical axis generally aligns with the axis, the endoscope may omit the optical folding arrangement. Moreover, while the disclosed scopes have bent imaging paths, they do not have any degree of parallelism between the tool bore and the imaging path along the scope length. The juxtaposition of the tool bore and the imaging path within the scope substantially prevents a user from viewing the surgical site commensurate with the way the surgical tool approaches the site.

Historically, endoscopes are reusable devices. But as far as patient safety is concerned, reusable devices frequently pose a higher infection risk than disposable medical devices. For purposes of this disclosure, a "disposable" device or a device called "disposable" is defined as a device or portion of a device that is used once for a procedure and then discarded such that those of ordinary skill in the art would view discarding the device as reasonable given the overall benefits from avoiding device reviews. Alternatively, "disposable" encompasses devices that have components that are not or are not designed or are not certified to be re-sterilizable. A third configuration is a device that has one reusable part (usually the handle and its durable components) and one or more disposable components (usually surgical tools) that are used on a single patient. This type of device is called reposable.

A rigid endoscope system comprises the following: the endoscope itself, that is, a long, tubular metallic conduit that contains optics that extend from the proximal end in a handle to the distal viewing tip. A light source cable connects to the proximal end to provide light for viewing, and the resultant object image is carried proximally through a separate optical system (lenses), back to an external camera at the proximal end. Images may be processed and stored in the camera or sent to a monitor for viewing, after being processed in an external video processing box.

Traditional endoscopes can have problems: first is the failure of a component of a system, especially if it is a reprocessed scope, and second is the bulk or unwieldy nature of a system. Endoscopes are delicate instruments and can become damaged with repeated use, cleaning, or resterilization. Owing to the cost, most operating rooms (ORs) do not have many back-up scopes.

Optics are essential parts of endoscopes. But aside from improving optical quality, the essential elements used for transferring light from the source to the target and transferring the resultant image back to the camera have not changed much over time. Light and images are transferred by combinations of fiber-optic bundles, lenses, and mirrors.

Fiber-optic bundles can be cost-effective, but they can display optical artifacts from packing density that can worsen with length. For this reason, many rigid endoscopes use gradient-index (GRIN) lenses despite the cost, length, and rigidity typical of these lenses. Current technology limits the length that GRIN lenses can be economically produced.

Ergonomic or logistic problems frequently seen in the OR suite stem from having many cords. As the wired devices are used during the procedures, the cords inevitably entangle. Frequently, such tangling breaks surgical components during the procedure, causing an FDA-reportable incident. In some surgery cases, the fiber-optic light cable and camera power cord stretching from the equipment-laden tower to the patient table causes clutter and becomes a tripping or other safety hazard, especially with many operators and technicians working in a small OR. Lack of reasonable solutions to draping cables and cords within the OR calls for wireless connectivity within the OR. Cord clutter also interferes with the ability of the operator to manipulate the tools inside or alongside an endoscope.

In addition to endoscope use, set-up also carries inherent safety issues. The external light source box can get hot and cause burns if mishandled.

Additionally, damage or failure in a scope discovered during system set-up could trigger not only repair work, but if no back-up scopes were immediately available, it could also force conversion of a minimally invasive surgical procedure to an open surgical procedure with associated costs, complications, and patient discomfort.

Reusable endoscopes are cleaned, re-sterilized, and stored with great care. Scope use is tracked, and scopes are maintained and upgraded, as necessary. Education and training in scope care, as well as the actual cleaning, expend valuable staff time. Light source boxes for the scopes, although not as delicate, also need to be maintained as capital equipment. Their maintenance adds time and resource costs to hospital operations, as well. Thus, while any medical device could be discarded after a single use, in some cases doing so would be unreasonable to those of ordinary skill in the art.

Even with functioning components, device assembly still takes time.

If some endoscope system components were integrated and available as one device, these issues would disappear.

SUMMARY

In the first embodiment of the invention, the endoscope incorporates folded optics to maintain a 0° angle between the imaging axis and the tool bore access. The device uses a folded path to maintain a line of sight (0°) with the offset imaging axis providing space for an axial tool bore, such as an axial tool bore parallel offset from the imaging axis or an imaging axis parallel offset from an axial tool bore, allowing the tool bore and the imaging axis to coexist without interfering with each other. See FIG. 7. The tool bore, parallel to the line of sight, alleviates bending stresses on electrosurgical devices (cauterizing and transection tool) or other mechanical cutting, clamping, holding, or specimen removal tools, while in the bore.

The device facilitates endoscopic or robotic general, cardiac, thoracic, endovascular, urologic, gynecologic, colorectal, oncologic, endocrine, pediatric, head and neck, hand, metabolic, and bariatric laparoscopic surgery; and minimally invasive orthopedic and neurologic surgery procedures. Also, the device facilitates minimally invasive vascular access surgery procedures, such as vein transposition, arteriovenous fistula, or arteriovenous grafting procedures, as part of a dialysis access surgical procedure. It also facilitates minimally invasive vein or artery harvesting, as an adjunct to coronary artery bypass grafting (CABG) surgical procedures.

The endoscope of this invention allows a laparoscopic surgeon to capture and remove a specimen, without having to switch the endoscope out of the primary endoscope port (umbilical or periumbilical) and to maintain a line of sight, until the surgeon captures the specimen. Then the surgeon can simultaneously remove the specimen bag and scope through the primary endoscope port, without having to switch to a different endoscope in a different port to keep the organ and tools in view. Thus, the endoscope can remain in place during specimen capture and removal during surgery. The ability for the endoscope to remain in place allows for better specimen removal since the camera, organ, and specimen removal tool always view the site from the same direction during the specimen removal phase.

Specimen removal can be especially risky for cancerous tissue. If the specimen removal procedure is compromised, cancerous tissue can be spread throughout the site and perhaps further. The present endoscope decreases the amount of potentially cancerous tissue manipulation needed for the procedure by maintaining direct visualization throughout capture and removal. Direct visualization occurs without additional manipulation caused by relocating the endoscope during the procedure.

In ORs with a small footprint, floor space can be quickly taken up by a video tower and fluoroscopic x-ray equipment. This endoscope offers direct visualization with fewer cords going to a video tower. Also, direct visualization can place fluoroscopic guidance. Both benefits free-up floor space and decrease the need for expensive equipment. Also, replacing fluoroscopic guidance makes the procedure safer by reducing the amount of radiation received by the patient and surgeon. Direct visualization is possible because the folded optics maintain a convenient viewing angle and leave space for optimal tool bore placement.

Various invention embodiments supply a system having a self-contained endoscope. The endoscope can have a handle connected to a conduit; a power and control module disposed within the handle; a light module disposed within the conduit, within the handle, and electrically connected to the power and control module. The endoscope can also have an imaging module disposed within the handle and electrically connected to the power and control module and a video camera disposed within the handle optically connected to the imaging module and electrically connected to the power and control module.

In some of these embodiments, the light module employs coherent fiber bundles in one way or another, either a path comprised of fiber-optic bundles arranged coaxially around the image pathway or as a separate illumination channel (see FIG. 6). In these or other embodiments, the light module employs an LED or a high-intensity LED.

In some embodiments, the endoscope has a tool bore disposed parallel to the entire central endoscope axis, wherein the endoscope axis maintains a straight, linear path from the proximal end of the scope to the distal end of the scope. In some embodiments, the light module is offset to allow space for the tool bore to pass through the endoscope. In some embodiments, the imaging components are offset to allow space for the tool bore to pass through the endoscope. In these or other embodiments, the light module, or the coherent fiber (CF) bundles of the light module coaxially lie around the imaging module. The folded imaging module path or the light module path within the handle moves imaging module components to the outer portion of the endoscope, likewise, providing space for a central or off-central tool bore. Some embodiments with wireless capability employ a discrete base having a receiver or transceiver and a display.

DETAILED DESCRIPTION

Figure 1:
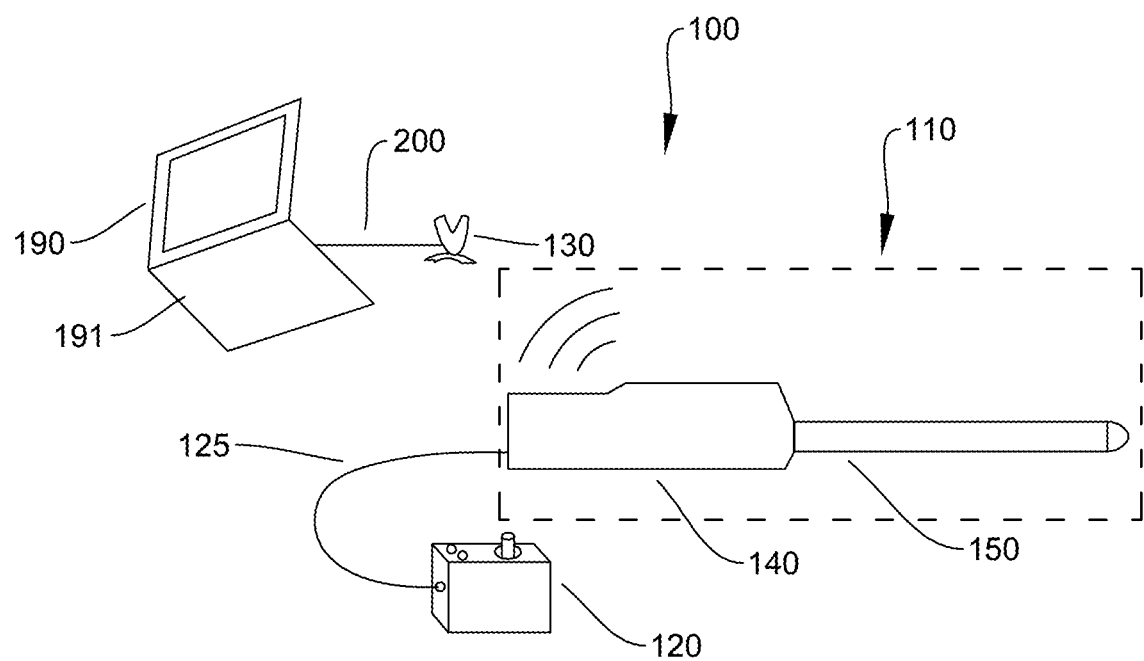
FIG. 1 is an overall system layout of an invention embodiment, showing the major components and their interconnections.

100 EN system
110 EN device
120 PCM
125 Cable
130 Receiver
140 Handle
143 T-slot
145 Cutout
146 Tool port
147 Tool bore
149 Ventilation openings
150 Conduit
151 Tip
160 Imaging module
161 lens
170 camera
180 Light module
182 waveguide pipe
182A optical fiber bundle
182B Circumferential single fiber bundle
190 Monitor
191 Base
200 Data cable or data line
201 Distal CF bundle
202 Proximal CF bundle
203-208 Optic elements
209-211 Dual-lens housings
212 Distal Imaging assembly (IA) end
213 Proximal IA end
214 Distal CF bundle distal end
215 Distal CF bundle proximal end
218 Proximal CF bundle distal end
219 Proximal CF bundle proximal end
220 S-curve
229 Coupler
230 Focus system
231 Imaging Plate
232 Wheel shaft
233 Focus wheel
235 Antenna
237 LED
238 Heat sink
239 wiring
244 Alignment rod
248 waveguide pipe tip
260 Imaging assembly
354 Battery
409, 410 Mirrors
411 EN device proximal end
412 EN Device distal end
572 Focal adjustment screw
573 Focal adjustment knob
774 data processing unit
775 Electrostatic shield
1147 Offset angle between imaging axis and tool bore axis
1260 imaging pipe
1271 Imaging Axis
1280 Tool Bore Axis
1409 Image Input
1410 Image Output
1420 angle between image input and image output
1430 electrical connection Unless defined otherwise, all technical and scientific terms used in this document have the same meanings that one skilled in the art to which the disclosed invention pertains would ascribe to them. The singular forms "a", "an", and "the" include plural referents unless the context clearly indicates otherwise. Thus, for example, a reference to "fluid" refers to one or more fluids, such as two or more fluids, three or more fluids, etc. Any mention of an element includes that element's equivalents as known to those skilled in the art.

Any methods and materials similar or equivalent to those described in this document can be used in the practice or testing of the present invention. This disclosure incorporates by reference all of the information of all of the publications mentioned in this disclosure.

The features, aspects, and advantages of the invention will become more apparent from the following detailed description, appended claims, and accompanying drawings.

This disclosure discusses publications only to facilitate describing the current invention. Their inclusion in this document is not an admission that they are effective prior art to this invention, nor does it indicate that their dates of publication or effectiveness are as printed on the document.

For purposes of this disclosure, "discrete" means lacking a physical connection to another object. For example, an object resting on the desk would be considered to be discrete from the desk. But if a screw connected the object to the desk, it would not be considered "discrete". Likewise, if an object were resting on the battery, it would be discrete from the battery, but if it were connected to the battery with electrical wiring, it would not be discrete. For purposes of this disclosure, "self-contained" means having all of the components necessary for operation. For example, a self-contained medical device would contain all of the components necessary for operating the medical device within the device itself. For purposes of this disclosure, "isolated" means not physically or electrically connected to another component of the system.

For purposes of this disclosure, "reposable" devices are devices designed to have portions that are disposable, and portions designed for reuse. In some versions of "reposable", the device is designed such that components that are more readily cleaned or sterilized after use, while less readily sterilized or cleaned components are not necessarily designed for reuse. In some versions, the more expensive components are designed to minimize the difficulty of reusing or sterilizing the device. In some cases, reposable devices include devices having been designed to facilitate reconditioning. In some cases, reposable devices are designed for limited reuse with 5 to 10 reuses.

It is expected that the disclosed system will make procedures simpler for the operator and, by extension, make the patient more comfortable. The devices are also expected to provide significant cost savings for the hospital on costly capital equipment (scope and light source) minimal maintenance costs, and associated costs with reprocessing the scope (staff time, cleaning, and sterilization costs) are eliminated.

The internal camera, wireless transmission of the image, and optics designed around a device configuration enabled the overall size of the device to be small. Compared with an assemblage of the cannula, camera, and associated cables and cords of a conventional system, a conduit with a handle is much more compact and therefore expected to be more comfortable for the operator to manipulate during the procedure and minimize cord entanglement.

System Components

FIG. 1 shows an example of an endoscope system 100 (EN). EN system 100 comprises EN device 110, cable 125, power and control module (PCM) 120, receiver 130, handle 140, conduit 150, monitor 190, base 191, and data cable 200. Imaging module 160, color camera 170, light module 180 are not shown in FIG. 1. In some embodiments, cable 125 is optional.

Figure 2:
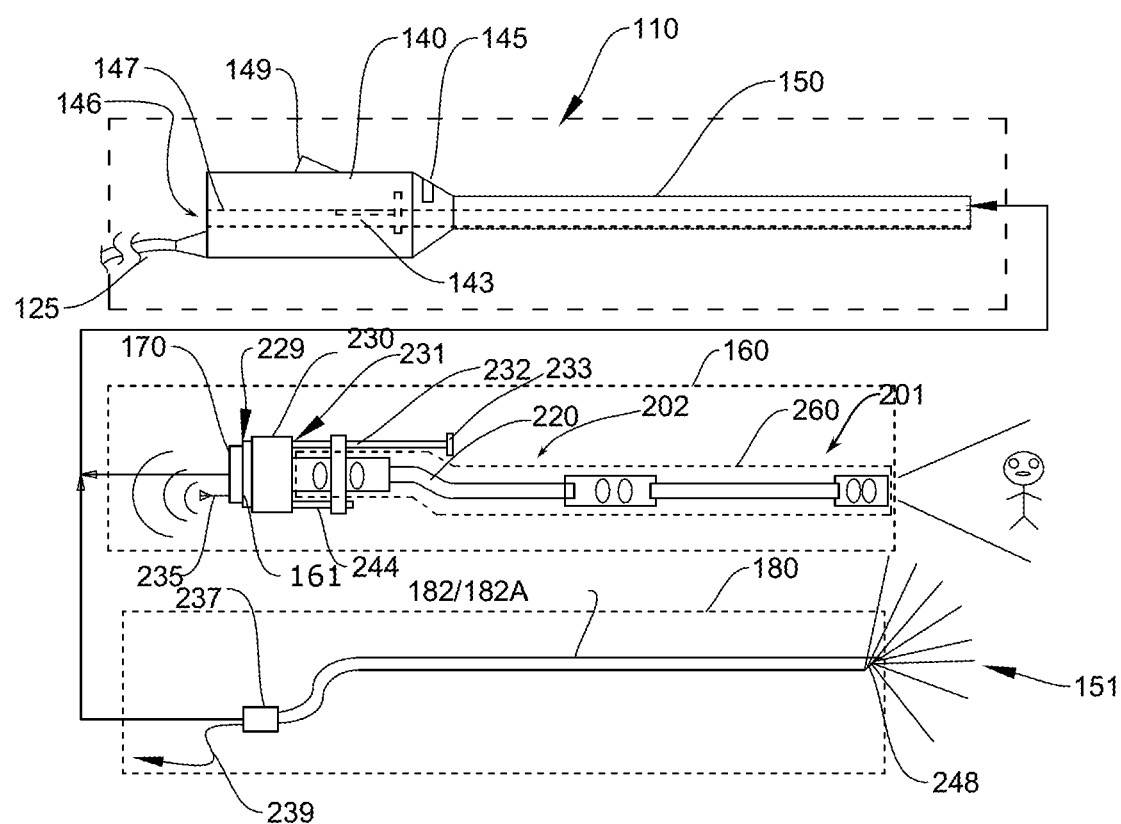
FIG. 2 depicts an embodiment of an endoscopic device (see FIG. 1).

FIG. 2 depicts an endoscope, otherwise called EN device 110. Housing 111 connects to conduit 150 with imaging module 160 extending through conduit 150 into housing 111. In some embodiments, the connection between handle 140 and conduit 150 is temporary, and in some embodiments, the connection is permanent. Handle 140 also connects to PCM 120 through cable 125 or wirelessly through antenna 235. Cable 125 provides an electrical supply to handle 140.

In the current invention, a system is described that integrates light module 180 and imaging module 160 into a single conduit-150-handle-140 assembly. In some embodiments, this integrated system is disposable.

FIG. 2 shows tool bore 147 offset or in parallel offset to imaging assembly 260. FIG. 2 also shows a version of light module 180, which comprises imaging module 160. Housing 111 has handle 140, handle body, end cap, T-slot 143, cutout 145, and tool port 146. T-slot 143 is used in some embodiments to receive a manipulation tool (not shown). Cutout 145 receives focus wheel 233.

In some embodiments, imaging module 160 or light module 180 are disposed against the inside wall of conduit 150. Moving the imaging module 160 and light module 180 up against the outer wall of conduit 150 facilitates passing a surgical instrument down the center of EN device 110. In some embodiments, the surgical device is coaxial with the EN device 110, such that rotation of EN device 110 can occur while the surgical device remains stationary.

As depicted in FIG. 2, imaging module 160 comprises lens 161, camera 170, alignment rod 244, wheel shaft 232, coupler 229, focus system 230, and imaging assembly (IA) 260. Imaging module 160 lies within housing 111. Coupler 229 connects focus system 230 to camera 170. Antenna 235 transmits a wireless signal to base unit 191.

In some embodiments, the outer diameter of conduit 150 (a stainless steel tube) is about 0.5 to 5.2 mm. In other embodiments, such components are about 12.7 mm OD and comprise internal bores for assorted surgical tools. The OD of conduit 150 is between 0.5 and 5.2 mm in diameter, in some embodiments. EVH-specific scopes sometimes use 12.7 mm OD and have internal ports for assorted surgical tools.

Focus system 230 comprises focus wheel 233, wheel shaft 232, plate 231, and alignment rod 244. Focus system 230 receives light representing an image at its distal end and focuses that image through coupler 229 onto imaging plate 231 or a detector. Focus wheel 233 changes the length of the focal elements inside of focus system 230 to cause the image to come into focus. Those of ordinary skill in the art are experienced with the construction and selection of focusing systems for endoscopes. As with imaging module 160, imaging assembly 260 lies within housing 111.

Also shown in FIG. 2, light module 180 comprises illumination pipe 182, LED 237, wiring 239, and illumination pipe tip 248. Light module 180 generates light, which travels across the transmissive joint through conduit 150 and projects past scope tip 151. Illumination light flows in illumination pipe 182. In some versions, Illumination pipe tip 248 at its distal end is cut and polished to render illumination pipe tip 248 non-imaging. This rendition comprises using tip 248 that has been cut and polished to a 30° angle. For purposes of this disclosure, the angle is measured relative to the longitudinal axis of illumination pipe 182. In other embodiments, this rendition comprises tip 248 that has been cut and polished perpendicular to the longitudinal axis of illumination pipe 182. An angle of 90° indicates a tip cut perpendicular to the longitudinal axis, and an angle of 30° indicates an angle 30° counterclockwise from the longitudinal axis, in the quadrant between 0° from the axis and perpendicular to the axis.

In some embodiments, illumination pipe 182 comprises 100 micron stepped-index multimode optical fiber bundles 182A enclosed in a circular close pack configuration at the proximal end, for light coupling efficiency. The fiber bundle passes through the device, then enters the annular gap between two concentric stain-less steel hypo tubes. The fibers are arranged circularly, for uniform light distribution at the distal end of the scope. In some versions, illumination pipe 182 comprises two fiber bundles.

In those embodiments that use an LED as the light source, LED 237 generates light that travels through illumination pipe 182 and projects out of illumination pipe tip 248 illuminating the region beyond tip 248. Sometimes LED 237 is a high-intensity device. Suitable high-intensity devices include a 6 mm SMD device, rated at 90 luminous flux (lm), such as a 1-watt unit available from OPTEK, or a high flux density LED, such as a Luxeon M device manufactured by Philips (Lumileds). High-intensity LED devices have a higher luminous flux, typically 900 (lm), and run hotter, requiring better heat dissipation. In some embodiments, the electrical input power operates near or above 3 watts.

In some embodiments, EN device 110 has a solid glass waveguide (3.0 mm Dia.), producing an illumination pattern offset from the imaging optical axis. This waveguide is positioned in a side-by-side configuration at the distal end of the scope body. In some embodiments, a fiber bundle is aligned in a circular configuration around the distal imaging lens. This circular configuration surrounding the imaging lens on the scope tip provides a uniform light distribution on the same optical axis as the imaging optics.

Some embodiments use software to connect or remove light reflected into imaging module 160 from body tissue or surgical tools. This software operates in real-time, within 250 milliseconds before being transmitted by the transmitter contained in the devices.

In some embodiments, proximal CF bundle 221 lacks the S-curve and is straight. Imaging assembly 260 couples to camera 170 through coupler 229. In the embodiment shown in FIG. 2, the proximal CF bundle 221 has S-curve 220 near its proximal end.

In some versions, EN device 110 comprises an identifier. The identifier may be wired or wireless. In another embodiment of the invention, the identifier may include a Radio Frequency Identification (RFID) tag, or some other integrated-circuit-based identifier mounted anywhere on or otherwise associated with EN device 110. In another embodiment of the invention, the identifier may include a resistor mounted on the EN device 110. In some of these embodiments, the sensor-identifier interaction causes hardware or software to refuse to power EN device 110, such as when the PCM 120 determines that an operator is attempting to reuse EN device 110 inappropriately.

As shown, light module 180 uses CF bundles made up of optical fibers 182A with optical fibers 182A associated with imaging assembly 260. Both imaging assembly 260 and light module 180 are sharply offset toward the inner wall of conduit 150, but in this arrangement, use up less interior space within conduit 150.

Figure 3:
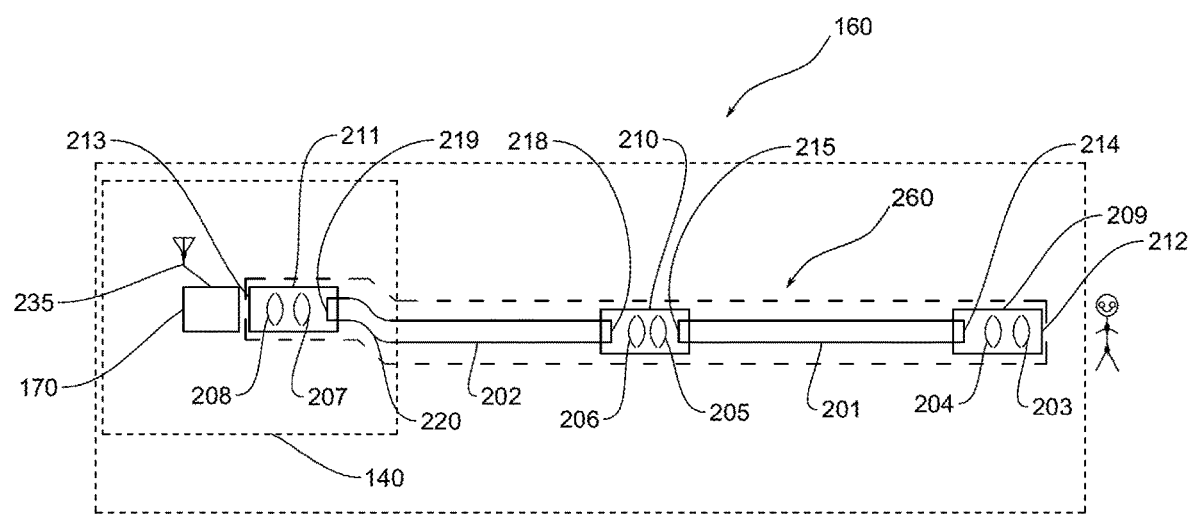
FIG. 3 depicts an embodiment of the imaging assembly.

FIG. 3 depicts an embodiment of an imaging assembly 260 that is part of EN device 110. Imaging assembly 260 comprises two, segmented, CF bundles 201 and 202, six achromatic optic elements 203 through elements 208, and three dual-lens housings 209, 210, and 211. Segmented CF bundles (201 and 202) comprise fiber segments of a length and diameter appropriate to fit EN device 110 in FIG. 2. CF bundles (201 and 202) relay an image of the target through close-packed fibers while maintaining image orientation.

Each of the optics elements (203 through 208) comprise different classes and exhibit different grind radiuses to counter spherical and chromatic aberrations of the image. The image first impinges on distal IA end 212. Achromatic optics elements 203 and 204 lie within dual-lens housing 209 and transfer and focus the image at distal IA end 212 to CF bundle 201 distal end 214.

Distal CF bundle 201 extends from dual-lens housing 209 to dual-lens housing 210. Distal CF bundle 201 transfers the image to the proximal end 215 of distal CF bundle 201. The second of the dual-lens housings 210 contains optic elements 205 and 206. These two optic elements (205 and 206) have focal lengths that project the image located at the proximal end 215 to distal end 218 of proximal CF bundle 202 without substantial distortion. This coupling technique is known as Free Space Optical Coupling. The number of optical elements, lens housings, etc. is exemplary only and will rise or fall as the optical design dictates.

Optic elements 207 and 208 are inside of dual-lens housing 211 and are similar to the optic elements contained in dual-lens housings 209 and 210. But the magnification levels of optic elements 207 and 208 can be changed to adjust the size of the image as it is viewed on a video monitor or display 190. Proximal CF bundle 202 transfers the image from distal end 218 to proximal end 219. Optic elements 207 and 208 have focal lengths that project the image at the proximal end 219 to proximal IA end 213. The image at proximal IA end 213 couples to camera 170 using coupler 229 (see FIG. 2).

Figure 4:
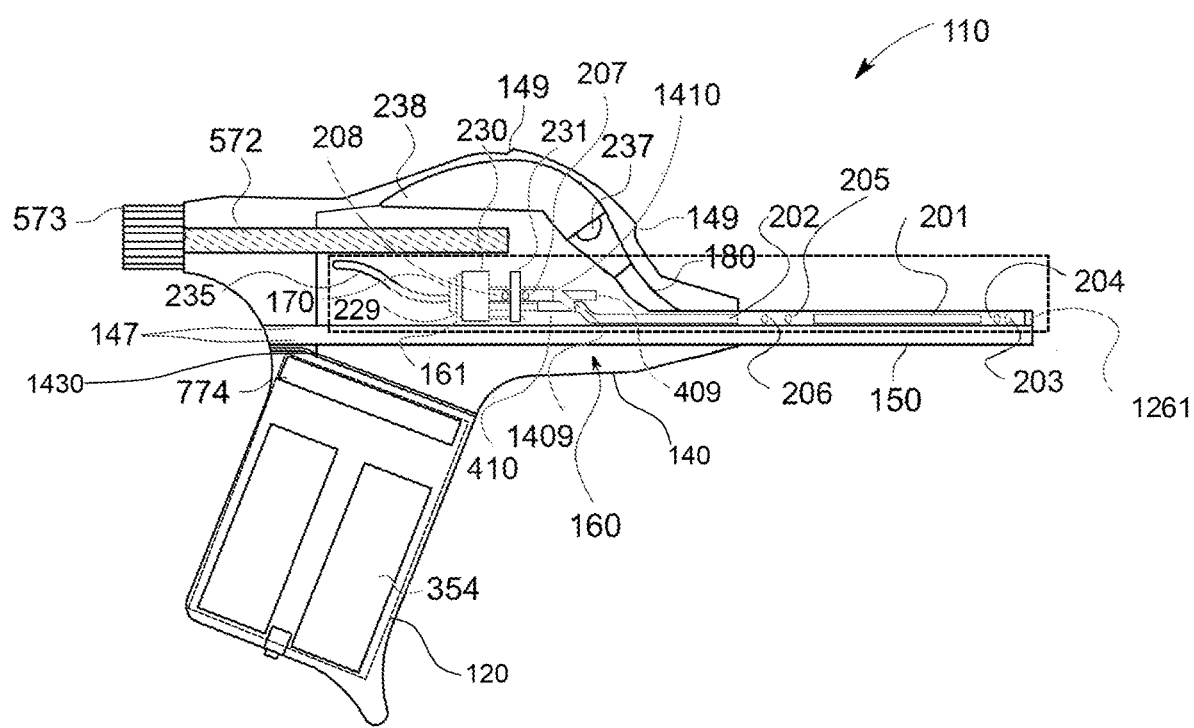
FIG. 4 depicts an overall system layout of an invention embodiment, showing the major components and their interconnections in a pistol-grip design.

FIG. 4 also depicts EN device 110. In this version, the components are inside of pistol-grip handle 140. Housing 111 connects to conduit 150. Imaging module 160 extends through conduit 150 into housing 111. In this case, imaging module 160 comprises proximal achromatic lens 161. Proximal achromatic lens 161 focuses an image transmitted along the conduit imaging module 160 on to color camera 170. Light module 180 also extends through conduit 150 into housing 111. Light module 180 bends out of the path of imaging module 160 once light module 180 enters housing 111. In this embodiment, light module 180 uses coherent optical fibers to transmit light from the housing to the tissue at the distal end of conduit 150. As can be seen, LED 237 produces light for the endoscope in this embodiment. In some embodiments, LED 237 connects to finned heat sinks 238 that remove heat that is generated by LED 237. Housing 111 also contains ventilation opening 149. The components in handle 140 wirelessly connect to PCM 120 using antenna 235.

Color camera 170 is attached to the focusing mechanism comprising focal assembly adjustment screw 572 and focusing adjustment knob 573. Manipulation of knob 573 causes color camera 170 to move laterally, adjusting the distance between camera 170 and lens 161. This embodiment has optical data processing unit 774 and is powered by batteries 354. This figure also shows antenna 235, which facilitates transmission of optical data from the endoscope to discrete base unit 191.

Figure 5:
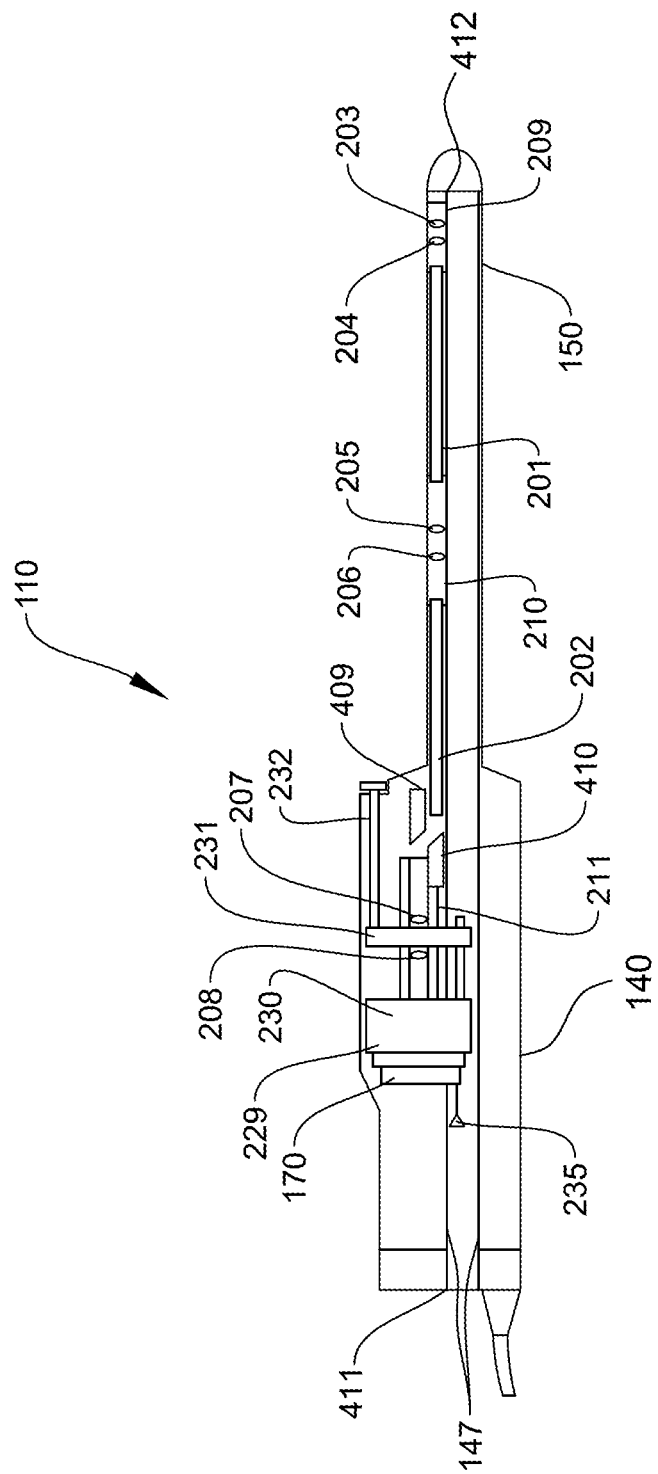
FIG. 5 depicts an embodiment of a self-contained endoscope having a bent or folded optical path in the imaging module and a parallel offset tool bore.

FIG. 5 details a partial assembly of an embodiment of EN device 110 that has a dual-folded imaging module 160. The folding occurs within handle 140 and allows EN device 110 to be more compact and allows imaging module 160 to avoid or clear the central axis of EN device 110. The clearance that flows from folding imaging module 160 facilitates a low-friction path, such as tool bore 147, through EN device 110, which accepts a surgical device in some embodiments. The surgical device enters the proximal end 411 of EN device 110. In these types of embodiments, camera 170, coupler 229, focusing mechanism components (230, 231, 232, 233), mirrors (409, 410), imaging system components (201-210) and lens housing 211 have been shifted off-center of handle 140. In this embodiment, a mirror assembly having two 45-degree mirrors 409, 410, allows folding without substantial degradation of an image. The image light enters an image input 1409 and exits an image output 1410 in the mirror assembly. In some versions, the image input lies at an angle relative to the image output. For instance, this angle can be zero to half of a degree, 0 to 10, or 0 to 5 degrees.

Figure 6A:
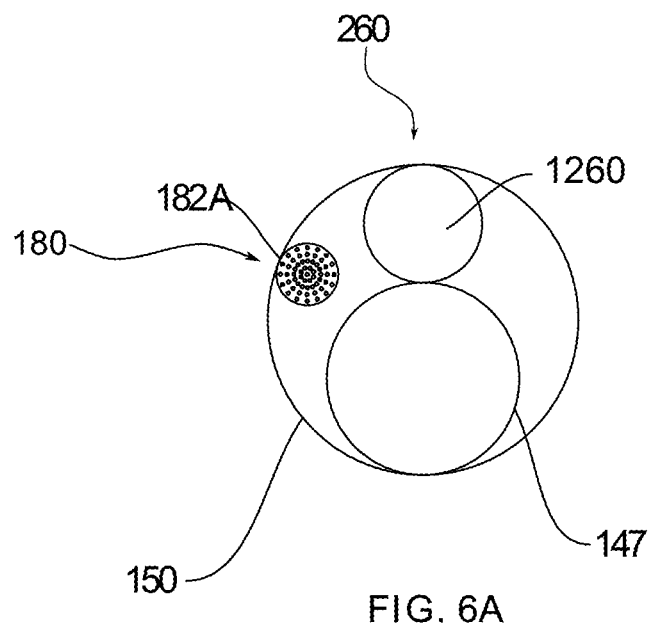
FIGS. 6A-C show cross-sections of various embodiments and endoscope conduit.
Figure 6B:
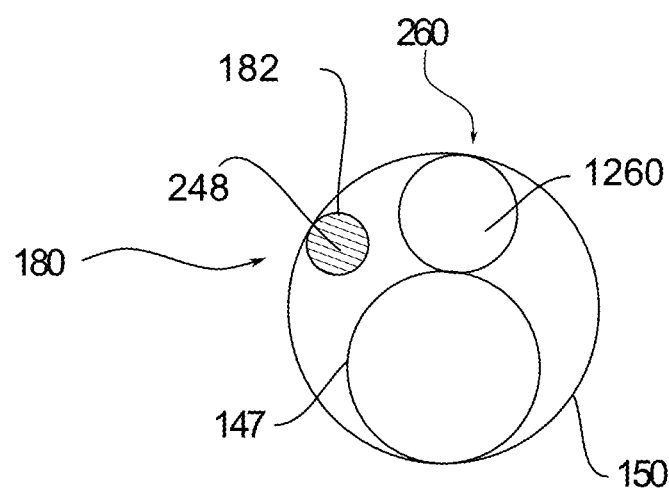
Figure 6C:
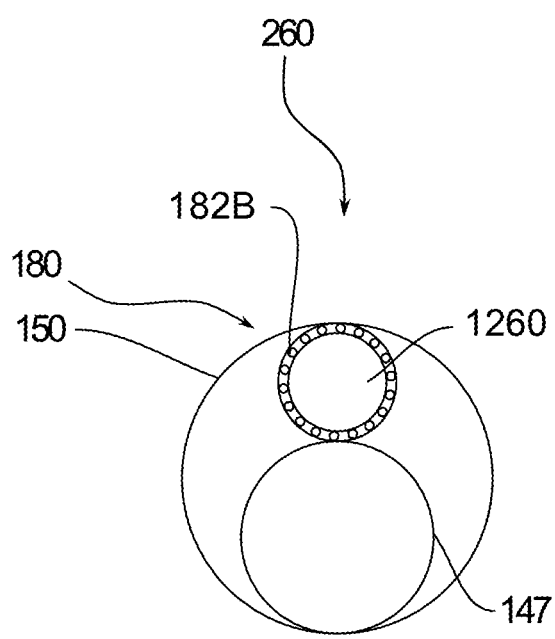

FIGS. 6A-C show various embodiments of conduit 150 in cross-section. FIG. 6A depicts conduit 150 substantially coaxially around tool bore 147. Imaging assembly 260 in this embodiment uses an imaging pipe 1260 for transmitting light representing image data from the distal end of EN device 110. Likewise, light module 180 uses illumination pipe 182 in this embodiment. Both imaging assembly 260 and light module 180 are sharply offset toward the inner wall of conduit 150 such that both clear the central region, leaving space in the central region for tool bore 147. In other versions, imaging assembly 260 and light module 180 skirt each other. Tool bore 147 can have dimensions that accommodate a discrete surgical device or tool.

FIG. 6B depicts conduit 150 substantially coaxially around tool bore 147. Imaging assembly 260 in this embodiment uses an imaging pipe 1260 for transmitting light representing image data from the distal end of EN device 110. Likewise, light module 180 uses CF bundles made up of optical fibers 182A in this embodiment. As for FIG. 6A, imaging assembly 260 and light module 180 are sharply offset toward the inner wall of conduit 150 such that both clear the central region, leaving space in the central region for tool bore 147.

FIG. 6C shows an embodiment with even more central-region space savings. This figure depicts conduit 150 substantially coaxially around tool bore 147, as before. Imaging assembly 260 in this embodiment uses an imaging pipe 1260 for transmitting light representing image data from the distal end of EN device 110. But in this case, light module 180 is disposed coaxially around imaging assembly 260. As shown, light module 180 uses CF bundles made up of optical fibers 182B with the optical fibers 182B substantially forming a ring around imaging assembly 260. Both imaging assembly 260 and light module 180 continue to be sharply offset toward the inner wall of conduit 150, but in this arrangement, use up even less interior space within conduit 150.

If an alternative source of relay optical conduits is used, such as GRINs, no post imaging processing is needed to remove the artifacts. But generally, GRINs are more expensive than CF bundles.

The small artifacts, caused by the spaces between the drawn optical fibers ($\approx$5-10 microns), can be removed by the use of image processing software, without compromising the integrity of the image.

Figure 7:
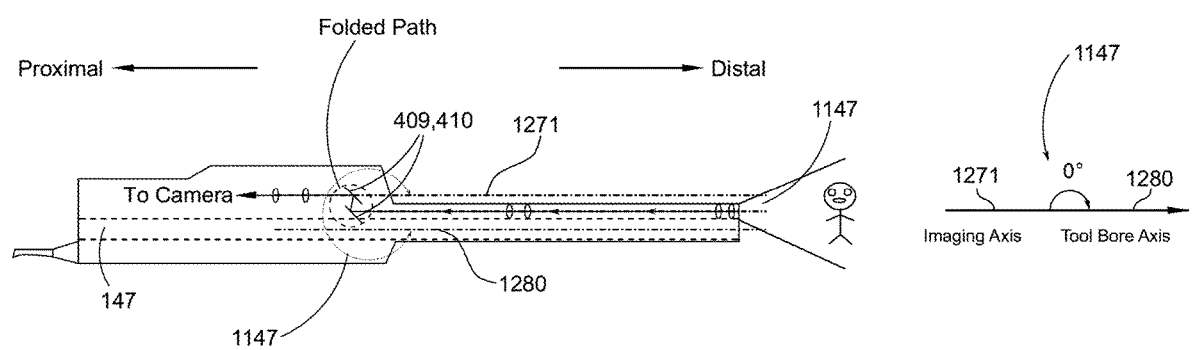
FIG. 7 shows the folded imaging pathway maintaining a 0° overall angle between the imaging axis and the tool bore axis.

FIG. 7 shows some of the terminology used in this disclosure and illustrates the folded path. The overall angle between the imaging axis and the tool bore is shown as zero degrees in this figure. Element 1147 represents the angle that the image input lies at with respect to the image output. Depending upon the embodiment, this angle is 0 to 10 or 0 to 5 degrees.

Operation

In operation, PCM 120 powers EN device 110 with EN Device 110 receiving power through cable 125. At an appropriate time, PCM 120 provides signals to light module 180 to cause appropriate or chosen lighting levels to be generated by LED 237. The light from LED 237 travels down illumination pipe 182 and projects out of illumination pipe tip 248, illuminating the field near illumination pipe tip 248. Either before or after turning on light module 180, handle 140 and conduit 150 are inserted into a patient's body, either using or not using a trocar to aid insertion.

EN device 110 projects light from light module 180 onto bodily tissue. That light reflects off of the tissue forming an image.

The image is projected into imaging module 160, as described above. Ultimately, the image impinges on a sensor or plate, after which, camera 170 transmits the image data. Once the image data is within base unit 191, the data is displayed on monitor 190.

Conduit 150 is inserted into the patient, and once the conduit is positioned at the desired location, the operator turns on LED 237. Light module 180 projects LED light along light module 180 out of the end of conduit 150, thereby illuminating the internal surgical compartment that is generally insufflated and expanded with $CO_2$ gas. For some high-intensity versions of LED 237, extra heat is conducted away from LED 237 by finned heat sinks 238 and out of housing 111 partially through ventilation opening 149. Light from light module 180 reflects off of the tissue forming an image. The image light enters imaging assembly 260 (part of imaging module 160). The optics of imaging assembly 260 conduct the image light up conduit 150 into housing 111. There, proximal achromatic lens 161 focuses the image light into camera 170, and camera 170 turns the photonic data into electrical data. Within camera 170 or optical data processing unit 774, various manipulations can be carried out on the image data, as desired.

When the image data does not arrive at camera 170 in focus, the operator can manipulate knob 573 to bring the image into focus. Rotation of knob 573 causes adjustment screw 572 to rotate, moving camera 170 longitudinally because camera 170 mounts on screw 572.

In some embodiments, EN device 110 is disassembled after use. For instance, in some embodiments, conduit 150, containing imaging module 160 through lens 161 and the portion of light module 180 ending just before LED 237, is removed for reconditioning or reprocessing, and the remainder of EN device 110 is discarded. In this type of embodiment, conduit 150 would be cleaned and sterilized and mounted within as yet unused EN device 110. This reprocessing can be carried out at the surgical facility or elsewhere.

While particular embodiments of the present invention have been shown and described, it will be obvious to those skilled in the art that changes and modifications can be made without departing from the embodiments of this invention in its broader aspects and, therefore, the appended claims are to encompass within their scope all such changes and modifications as fall within the true, intended, explained, disclose, and understood scope and spirit of this invention's multitudinous embodiments and alternative descriptions.

Additionally, various embodiments have been described above. For convenience's sake, combinations of aspects composing invention embodiments have been listed in such a way that one of ordinary skill in the art may read them exclusive of each other when they are not necessarily intended to be exclusive. But a recitation of an aspect for one embodiment is meant to disclose its use in all embodiments in which that aspect can be incorporated without undue experimentation. In like manner, a recitation of an aspect as composing part of an embodiment is a tacit recognition that a supplementary embodiment exists that specifically excludes that aspect. All patents, test procedures, and other documents cited in this specification are fully incorporated by reference to the extent that this material is consistent with this specification and for all jurisdictions in which such incorporation is permitted.

Moreover, some embodiments recite ranges. When this is done, it is meant to disclose the ranges as a range, and to disclose each and every point within the range, including end points. For those embodiments that disclose a specific value or condition for an aspect, supplementary embodiments exist that are otherwise identical, but that specifically exclude the value or the conditions for the aspect.

What is claimed is:

1. An endoscope system comprising an endoscope having a handle with an in-line configuration or alternatively with a pistol grip configuration;
a conduit extending distally from the handle;
wherein the conduit contains a light module for illumination of a target, an imaging assembly to transmit an image of the target to a camera, and a tool bore;
an electrical power and control module (PCM) in the handle;
an LED light source in the handle, connecting to the PCM;
wherein
the light module contains the LED light source, which connects to a glass illumination pipe that transmits light to the target;
and
the imaging assembly comprises distal and proximal segmented coherent fiber (CF) bundles with three pairs of optic elements (achromatic lenses), each pair contained in separate dual-lens housings in the conduit and the handle, with pairs at the distal and proximal ends of the imaging assembly and one pair intermediate between the distal and proximal CF bundles; the proximal pair of optic elements is optically connected to a CCD chip contained in the camera.

2. The endoscope system of claim 1, wherein the tool bore extends in a straight line coaxially or eccentrically through the endoscope with the imaging assembly running in parallel offset to the tool bore.

3. The endoscope system of claim 2, wherein the imaging assembly comprises a mirror assembly.

4. The endoscope system of claim 3, wherein the mirror assembly further comprises an image input and an image output.

5. The endoscope system of claim 4, wherein the image input lies at an angle relative to the image output.

6. The endoscope system of claim 5, wherein the angle is 0 to 10 or 0 to 5 degrees.

7. The endoscope system of claim 6, wherein the angle is zero to half of a degree.

8. The endoscope system of claim 7, wherein the illumination pipe comprises an illumination fiber bundle disposed coaxially around the imaging assembly.

9. The endoscope system of claim 8 wherein the camera connects to the imaging assembly and the PCM.

10. The endoscope system of claim 9, wherein the tool bore extends along or parallel to a central endoscope axis, as defined by the conduit.

11. The endoscope system of claim 10, wherein the image assembly has coaxially arranged light fibers and adjoins the tool bore.

12. The endoscope system of claim 1, wherein the imaging assembly is folded thereby providing folded optics in the handle.

13. The endoscope system of claim 12, wherein the distal and proximal segmented coherent fiber bundles are in-line segmented bundles.

14. A method comprising:
providing the endoscope system of claim 3;
inserting the endoscope into a patient;
and
inserting a surgical tool into the tool bore.

15. The method of claim 14 further comprising viewing a surgical site inside the patient.

16. The method of claim 15 further comprising executing a surgical procedure at the surgical site.

17. The method of claim 16 further comprising removing the surgical tool from the tool bore.

* * * * *